(12) United States Patent
Cai et al.

(10) Patent No.: US 11,707,552 B2
(45) Date of Patent: Jul. 25, 2023

(54) PREPARATION METHOD OF BIOMEDICAL TITANIUM IMPLANT WITH FUNCTION OF ELIMINATING SURFACE BIOMEMBRANE

(71) Applicant: CHONGQING UNIVERSITY, Chongqing (CN)

(72) Inventors: Kaiyong Cai, Chongqing (CN); Zhang Yuan, Chongqing (CN); Peng Liu, Chongqing (CN)

(73) Assignee: CHONGQING UNIVERSITY, Chongqing (CN)

( * ) Notice: Subject to any disclaimer, the term of this patent is extended or adjusted under 35 U.S.C. 154(b) by 216 days.

(21) Appl. No.: 17/272,978

(22) PCT Filed: Jun. 4, 2020

(86) PCT No.: PCT/CN2020/094456
§ 371 (c)(1),
(2) Date: Mar. 3, 2021

(87) PCT Pub. No.: WO2020/244600
PCT Pub. Date: Dec. 10, 2020

(65) Prior Publication Data
US 2021/0220520 A1 Jul. 22, 2021

(30) Foreign Application Priority Data
Jun. 6, 2019 (CN) .......................... 201910491004.7

(51) Int. Cl.
*B05D 1/18* (2006.01)
*A61L 27/44* (2006.01)

(52) U.S. Cl.
CPC .............. *A61L 27/446* (2013.01); *B05D 1/18* (2013.01); *A61L 2400/12* (2013.01); *A61L 2420/02* (2013.01)

(58) Field of Classification Search
CPC ....................................................... B05D 1/18
See application file for complete search history.

(56) References Cited

FOREIGN PATENT DOCUMENTS

| CN | 1901801 | 1/2007 | | |
|---|---|---|---|---|
| CN | 104195617 | 12/2014 | | |
| CN | 106512083 | 3/2017 | | |
| CN | 108853604 | 11/2018 | | |
| CN | 108853604 A | * 11/2018 | ........... | A61L 31/028 |
| CN | 109453398 | 3/2019 | | |
| CN | 110464783 | 11/2019 | | |
| WO | 2007/089084 | 8/2007 | | |

* cited by examiner

*Primary Examiner* — Tabatha L Penny
(74) *Attorney, Agent, or Firm* — JMB Davis Ben-David

(57) ABSTRACT

The present invention discloses a preparation method of a biomedical titanium implant with a function of eliminating a surface biomembrane. The method includes the following steps: firstly synthesizing mesoporous polydopamine (MPDA) nanoparticles by a "one-pot method", constituting a surface-aminated titanium material through diacid corrosion and modification of a 3-aminopropyltriethoxysilane (APTES) coupling agent, and integrating the MPDA nanoparticles into the surface of the titanium material through Michael addition reaction; secondly, taking MPDA anchored on the surface of the titanium material as a photothermal material and a photosensitizer carrier, where MPDA contains abundant aromatic rings capable of facilitating abundant loading of a photosensitizer (indocyanine green, ICG) through π-π stacking interaction; and finally further modifying biocompatible RGD polypeptides on the surface of MPDA by Michael addition reaction, where a modified titanium material is referred to as Ti-M/I/RGD.

10 Claims, 5 Drawing Sheets

PREPARATION METHOD OF BIOMEDICAL TITANIUM IMPLANT WITH FUNCTION OF ELIMINATING SURFACE BIOMEMBRANE

CROSS-REFERENCE TO RELATED APPLICATIONS

This is the U.S. National Stage of International Patent Application No. PCT/CN2020/094456 filed on Jun. 4, 2020, which in turn claims the benefit of Chinese Patent Application No. 201910491004.7 filed on Jun. 6, 2019.

TECHNICAL FIELD

The present invention relates to the field of biomedical materials, and in particular, to a preparation method of a biomedical titanium implant with a function of eliminating a surface biomembrane.

BACKGROUND

Bacterium are prone to organize themselves into viscous and powerful multicellular communities referred to as a biomembrane capable of withstanding a host immune system, antibiotics and environmental pressure. Clinically, infections associated with bone implantation are mainly caused by bacterium in the biomembrane, rather than by suspended bacterium that grow in suspension. Once the biomembrane is formed, an implant replacement surgery is inevitable, which brings a heavy economic burden to the patient. So far, there have been many substantial surface modification strategies, which are used for preventing the biomembrane from formation or damaging the formed biomembrane, such as an anti-adhesion interface, as well as an integration interface of antibiotics, antibacterial peptides, silver nanoparticles and DNA enzyme I. However, in some special circumstances, the invalid antibacterial interface of the implant may still cause bacterial infection and even the formation of the biomembrane. Therefore, it is an urgent need to develop some non-surgical or non-invasive treatment methods against the biomembrane that has been formed on the implant.

In recent years, a photothermal therapy (hereafter referred to as PTT) triggered by near-infrared lights has gained increasing concerns in the field of nanomedicine due to minimal invasiveness, deeper tissue penetration and relatively high selectivity. Moreover, the PTT is considered as a promising antibacterial strategy, which can convert light energy into local heat energy to destroy the integrity of bacterium or the structure of the biomembrane. However, relatively high local temperature is required to kill bacterium only by using the PTT, and this may cause damage to tissues. Therefore, it is particularly worth considering a synergistic application of the PTT and other antibacterial strategies, and this has a significant effect on inhibiting bacterial infections or eliminating the establishment of the biomembrane. A photodynamics therapy (hereafter referred to as PDT) is a potential antibacterial strategy. Reactive oxygen species (hereafter referred to as ROS) generated by the PDT destroy the integrity of bacterial membranes, so that the removal efficiency of the biomembrane can be significantly improved by safe PTT temperature.

However, good resistance to the biomembrane and potential cytotoxicity are concurrent. Therefore, it is an urgent to-be-solved problem to conduct the surface modification of a titanium-based implant material and provide an elimination capability for a non-replaceable biomembrane of a titanium implant and an osseointegration performance after biomembrane elimination.

SUMMARY

The purpose of the present invention is to provide a preparation method of a biomedical titanium implant with a function of eliminating a surface biomembrane, and the method includes the following steps.

1) Synthesizing mesoporous polydopamine (MPDA) nanoparticles by a "one-pot method".

1.1) Weighing polyoxyethylene polyoxypropylene (PLURIONIC® F127 poloxamer) into a reactor; weighing trimethylbenzene (TMB) into a reaction flask; pouring distilled water and ethanol in sequence; and then stirring a mixture of distilled water and ethanol at ambient temperature.

1.2) Dissolving dopamine hydrochloride and trismetylaminomethane (Tris) in the distilled water; adding the dissolved mixture to the mixed solution of Step 1.1); and making the dissolved mixture fully react with the mixed solution at ambient temperature.

In Steps 1.1) to 1.2), the ratio of the mass (mg) of polyoxyethylene polyoxypropylene to the volume (mL) of trimethylbenzene to the volume (mL) of the distilled water in Step 1.1) to the volume (mL) of ethanol to the mass (mg) of dopamine hydrochloride to the volume (mL) of trismetylaminomethane to the volume (mL) of the distilled water in Step 1.2) is (2000-4000):(2-5):(500-1000):(500-1000):(200-800):(200-1000): 100.

1.3) Carrying out centrifugal treatment on a product prepared after reaction in Step 1.2), where sediments prepared through centrifugal treatment are non-mesoporous polydopamine nanoparticles; dispersing the nanoparticles in a mixture of ethanol and acetone; removing a template through sonication; and collecting prepared mesoporous polydopamine nanoparticles through centrifugation.

In the Step, the ratio of ethanol to acetone is 1:(1-3).

2) Forming a large number of hydroxyl groups on the surface of the titanium material by diacid corrosion, and further modifying the surface of the titanium material through amination.

2.1) Preparing a hydrofluoric acid solution with a concentration of 0.1%-0.5% and a sulfuric acid solution with a concentration of 50%-70%; mixing the hydrofluoric acid solution with the sulfuric acid solution (HF:H2SO4) according to the ratio of (1-2):(1-2) to prepare a diacid solution; placing a titanium foil into the diacid solution; and making the titanium foil fully react with the diacid solution to prepare a titanium material with a large number of hydroxyl groups on the surface thereof.

2.2) Soaking the titanium material prepared by Step 2.1) in a solution of 3-aminopropyltriethoxysilane (APTES) with a concentration of 1%-5%; and making the titanium material fully react with the solution to prepare a aminated titanium material.

3) Integrating the MPDA nanoparticles into the surface of the aminated titanium material through Michael addition reaction.

3.1) Dispersing the mesoporous polydopamine nanoparticles prepared by Step 1.3) into Tris-HCl with a pH value of 7-9, to prepare an MPDA solution with a concentration of 1-5 mg/mL.

3.2) Soaking the aminated titanium material prepared by Step 2.2) in the MPDA solution and making the aminated titanium material react with the MPDA solution for 12-24 hours, to prepare a Ti-M substrate.

4) Integrating RGDC polypeptides on the surfaces of the MPDA nanoparticles through Michael addition reaction and loading a photosensitizer ICG into MPDA on the surface of the titanium material through π-π stacking interaction.

4.1) Preparing a 1-5 mg/mL RGDC polypeptide solution, and taking a Tris-HCl solution with a pH value of 7-9 as a solvent; soaking the Ti-M substrate prepared by Step 3.1) in the RGDC solution; and making the Ti-M substrate fully react with the RGDC solution, to prepare a Ti-M/RGD substrate.

4.2) Preparing a 2-20 μg/mL indocyanine green (ICG) solution with distilled water as a solvent; soaking the Ti-M/RGD substrate prepared by Step 4.1) in the ICG solution, making the Ti-M/RGD substrate fully react with the ICG solution, and finally preparing a non-invasive functional titanium material for eliminating the biomembrane and accelerating bone formation with a photothermal/photodynamic effect triggered by a long-range near-infrared light (NIR), where the titanium material is referred to as Ti-M/I/RGD.

Further, in Step 1), synthesizing the mesoporous polydopamine (MPDA) nanoparticles by using the "one-pot method".

Further, in Step 1.1), stirring a mixture of distilled water and ethanol for 10-60 min at ambient temperature.

Further, the reaction processes in Step 1.2) are respectively carried out at ambient temperature, with the reaction time ranging from 6-24 h.

Further, in Step 1.3), sonication is carried out for 20-60 min to remove the template, and collection of sediments through centrifugation is repeatedly conducted 1-5 times to collect nanoparticles generated through centrifugation.

Further, in Step 2.1), the reaction temperature is in the range of 40-80° C., and the reaction time is in the range of 5-20 min.

Further, in Step 2.2), the size of the titanium foil is 10 mm×10 mm (which is cut according to the size of a culture plate used), and the reaction time is in the range of 12-48 h.

Further, in Steps 4.1) and 4.2), the reaction time is in the range of 12-24 h.

Further, different titanium materials in Steps 2.1), 2.2), 3.1), 4.1) and 4.2) are required to be rinsed with distilled water 3 times and dried at ambient temperature.

A titanium material prepared by the preparation method of the present invention is used for eliminating a biomembrane formed on the surface of the biomedical titanium implant based on a photothermal/photodynamic therapy strategy.

It is worth noting that the biomimetic material of polydopamine (PDA) inspired by mussels has been widely used in the field of biomaterials with the advantages of good biocompatibility, high near-infrared light-to-heat conversion efficiency, and convenience to functionalize. Studies show that PDA-related nanoparticles as photothermal materials have been widely applied to the development of anti-tumor photothermal agents. In addition, the PDA nanoparticles containing antibiotics increase the release of antibiotics when being exposed to near-infrared lights, trigger the photothermal effect of the PDA nanoparticles, and synergistically exert an efficient antibacterial effect. Recent studies show that the synergistic use of photothermal/photodynamics therapy is a promising strategy to kill bacterium and eliminate biomembranes.

In the study, the mesoporous polydopamine (MPDA) nanoparticles are synthesized by the "one-pot method" and integrated into the surface of the aminated titanium material through Michael addition reaction; the MPDA nanoparticles on the titanium material can be used as a drug reservoir through π-π stacking, to further adsorb the photosensitizer ICG; MPDA can still modify the biocompatible RGDC polypeptides on the surface through Michael addition reaction, and the titanium material finally constituted is referred to as Ti-M/I/RGD.

It is speculated that under the near-infrared lights, Ti-M/I/RGD is triggered to generate local high temperature under which ICG is released and diffused into the biomembrane; at the same time, the near-infrared lights stimulate the photosensitizer ICG to generate lots of reactive oxygen species by which the structure of the bacterial membrane is destroyed, so that the bacterial membrane is more sensitive to high temperature; finally, the local high temperature caused by triggering MPDA with near-infrared lights eventually leads to the death of the biomembrane. In addition, after the biomembrane on the surface of the titanium implant is removed, a good osseointegration effect is still present due to the existence of the RGDC polypeptides. Therefore, the study proposes a feasible in-vivo anti-biomembrane strategy. Based on a PDT/PTT effect triggered by NIR, the biomembrane formed on the surface of the titanium material is eliminated in vivo through a remote controllable method, instead of a surgical or invasive therapy.

The technical effect of the present invention is beyond doubt, and the present invention has the following advantages.

1) No special equipment is provided in the preparation method, and the preparation method is simple to operate, and has strong controllability.

2) In the present invention, a preparation method of a titanium material constituted based on a photothermal/photodynamics therapy strategy and used to non-invasively eliminate the implant surface biomembrane has an important research value and clinical significance in the application of antibacterial implant materials.

DESCRIPTION OF DRAWINGS

FIG. 2a (scale bar=2 μm) is a scanning electron micrograph of a Ti surface subject to diacid corrosion; FIGS. 2b (scale bar=2 μm) and 2c (scale bar=400 nm) are a scanning electron micrograph of a Ti-M surface subject to integration of MPDA nanoparticles.

FIG. 4a is a consumption chart of DPBF of an ROS detection probe of a Ti substrate exposed to near-infrared lights; FIG. 4b is a consumption chart of DPBF of an ROS detection probe of a Ti-M/I/RGD substrate exposed to near-infrared lights.

DESCRIPTION OF EMBODIMENTS

Figure 1:
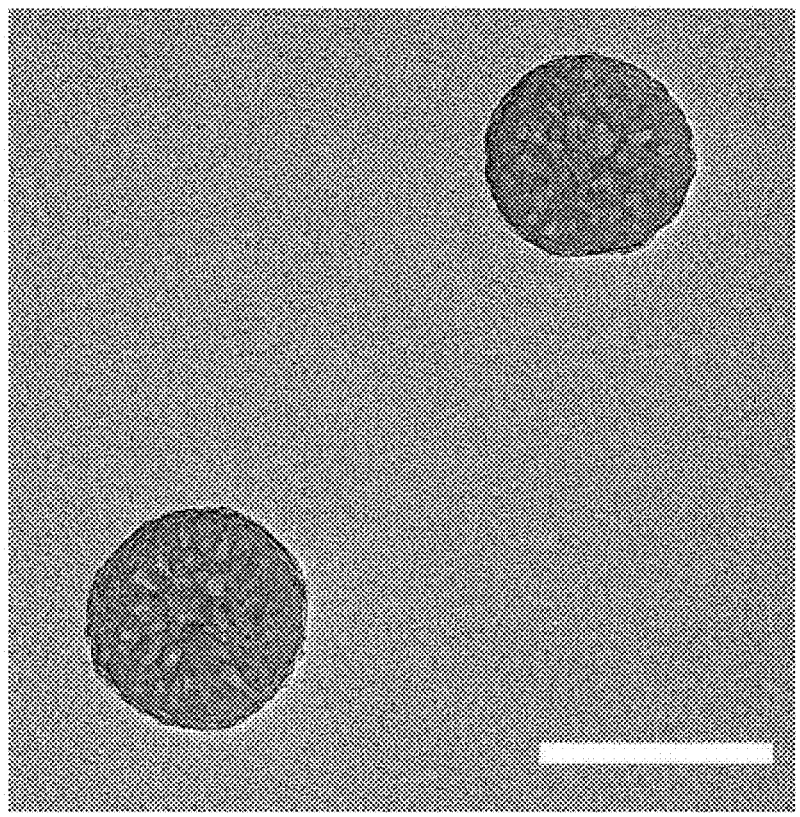
FIG. 1 is a transmission electron micrograph (scale bar=200 nm) of mesoporous polydopamine (MPDA) nanoparticles.

The following gives a further description for the present invention according to embodiments, but it should not be understood that the above subject of the present invention is only restricted to the following embodiments. Without departing from the above technical ideas of the present invention, various substitutions and modifications made based on common technical knowledge and conventional means in the art should be included within the protection scope of the present invention.

Embodiment 1

A preparation method of a titanium material for non-invasively eliminating an implant surface biomembrane based on a photothermal/photodynamic therapy strategy is provided, and the preparation method includes the following steps:

1) Synthesize mesoporous polydopamine (MPDA) nanoparticles by a "one-pot method".

1.1) Weigh 350 mg polyoxyethylene polyoxypropylene (PLURIONIC® F127 poloxamer) into a 250 mL reaction flask; weigh 400 μL trimethylbenzene (TMB) into a reaction flask; pour 60 mL distilled water and 65 mL ethanol in sequence; and then stir a mixture of distilled water and ethanol for 30 min at ambient temperature.

1.2) Dissolve 60 mg dopamine hydrochloride and 90 mg trismetylaminomethane (Tris) in 10 mL distilled water; add the dissolved mixture to the mixed solution of Step 1.1);

The reaction processes are respectively carried out at ambient temperature, with 24 h reaction time.

1.3) Carry out centrifugal treatment on a product prepared after reaction in Step 1.2), where sediments prepared through centrifugal treatment are non-mesoporous polydopamine nanoparticles. Sonicate the nanoparticles for 30 min in a 30 mL ethanol/acetone mixed solution to remove the template; collect sediments through repeated three-time centrifugation; and collect mesoporous polydopamine nanoparticles prepared through centrifugation.

2) Form a large number of hydroxyl groups on the surface of the titanium material by diacid corrosion, and further modify the surface of the titanium material through amination.

2.1) Prepare a hydrofluoric acid solution with a concentration of 0.2% and a sulfuric acid solution with a concentration of 66%; mix the hydrofluoric acid solution with the sulfuric acid solution in a specific volume ratio (HF:H2SO4=1:1) to prepare a diacid solution; place a titanium foil with the size of 10 mm×10 mm into the diacid solution; and make the titanium foil react with the diacid solution for 10 min at temperature of 80° C. to prepare the titanium material with a large number of hydroxyl groups on the surface;

2.2) Soak the titanium material prepared by Step 2.1) in a solution of 3-aminopropyltriethoxysilane (APTES) with a concentration of 3%; and make the titanium material fully react with the solution to prepare a aminated titanium material.

3) Integrate the MPDA nanoparticles into the surface of the aminated titanium material through Michael addition reaction.

3.1) Disperse the nanoparticles prepared by Step 1.3) into Tris-HCl with a pH value of 8.5, to prepare 2 mg/mL MPDA solution.

3.2) Soak the aminated titanium material prepared by Step 2.2) in the 2 mg/mL MPDA solution and make the aminated titanium material react with the MPDA solution for 24 hours, to prepare a Ti-M substrate.

4) Integrate RGDC polypeptides on the surfaces of the MPDA nanoparticles through Michael addition reaction and load a photosensitizer ICG into MPDA on the surface of the titanium material through π-π stacking interaction.

4.1) Prepare a 2 mg/mL RGDC polypeptide solution, and take a Tris-HCl solution with a pH value of 8.5 as a solvent; soak the Ti-M substrate prepared by Step 3.1) in the RGDC solution; and make the Ti-M substrate fully react with the RGDC solution for 24 h, to prepare a Ti-M/RGD substrate.

4.2) Prepare a 10 μg/mL indocyanine green (ICG) solution with distilled water as a solvent; soak the Ti-M/RGD substrate prepared by Step 4.1) in the ICG solution, make the Ti-M/RGD substrate fully react with the ICG solution for 24 h, and finally prepare a non-invasive functional titanium material for eliminating the biomembrane and accelerating bone formation with a photothermal/photodynamic effect triggered by a long-range near-infrared light (NIR), where the titanium material is referred to as Ti-M/I/RGD.

The product prepared by the above preparation method is considered as a titanium implant for non-invasively eliminating a surface biomembrane based on a photothermal/photodynamics therapy strategy.

FIG. 1 is a transmission electron micrograph (scale bar=200 nm) of mesoporous polydopamine (MPDA) nanoparticles, especially for a transmission electron micrograph of mesoporous polydopamine (MPDA) obtained after completion of Step 1). FIG. 1 shows that the diameter of the MPDA nanoparticles prepared in this embodiment is approximately 200 nm.

Figure 2:
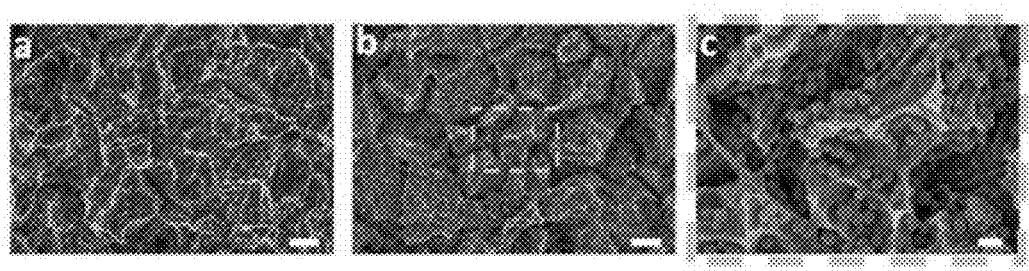
FIG. 2 is a scanning electron micrograph of Ti subject to diacid corrosion and a constituted Ti-M.

FIG. 2*a* (scale bar=2 μm) is a scanning electron micrograph of a Ti surface subject to diacid corrosion; and FIGS. 2*b* (scale bar=2 μm) and 2*c* (scale bar=400 nm) are a scanning electron micrograph of a Ti-M surface subject to integration of MPDA nanoparticles. Referring to FIG. 2*c*, it can be seen that the MPDA nanoparticles have been successfully integrated into the surface of the titanium material.

Figure 3:
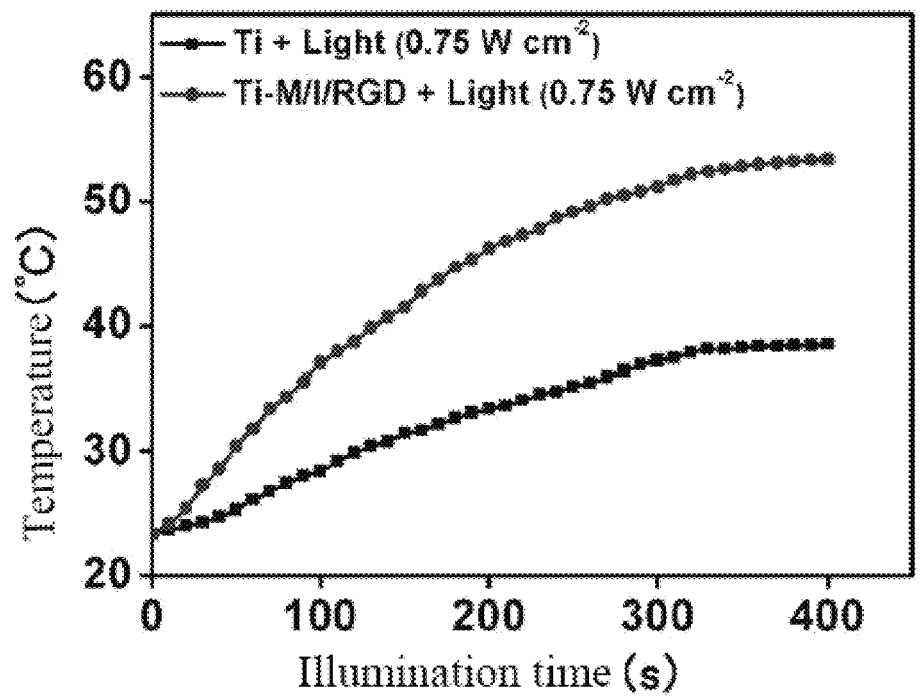
FIG. 3 is a surface temperature change curve of Ti and Ti-M/I/RGD substrates under near-infrared lights.

FIG. 3 is a temperature change curve of Ti and Ti-M/I/RGD substrates under near-infrared lights (0.75 W cm$^{-2}$). Referring to FIG. 3, it can be seen that the temperature of the Ti surface exposed for 600s rises from 23.3° C. to 39.2° C. and the temperature of the Ti-M/I/RGD surface rises from 23.3° C. to 54.2° C., which indicates the photothermal performance of the Ti-M/I/RGD substrate.

Figure 4:
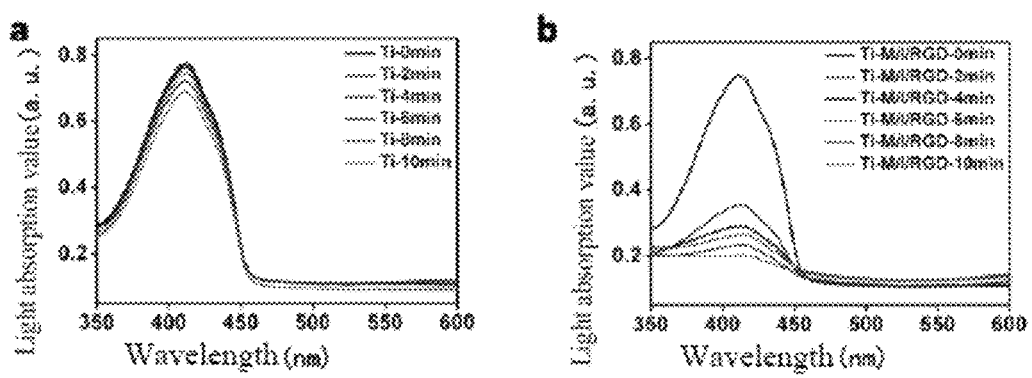
FIG. 4 is a comparison chart of ROS generated on Ti and Ti-M/I/RGD substrates under near-infrared lights.

FIG. 4 is a comparison chart of ROS generated on Ti and Ti-M/I/RGD substrates under near-infrared lights; FIG. 4*a* shows that DPBF on the ROS detection probe is not significantly consumed after the Ti substrate is exposed to near-infrared lights; FIG. 4*b* shows that DPBF on the ROS detection probe is significantly consumed after the Ti-M/I/RGD substrate is exposed to near-infrared lights, indicating the ability of the T/I/RGD substrate to generate ROS.

From the above, it can be proved that in the present invention, photothermal and ROS generation interfaces triggered by near-infrared lights have been successfully constituted on the titanium material.

In a constituting process, synthesis of mesoporous polydopamine (MPDA) nanoparticles, integration of MPDA nanoparticles on the titanium material surface, integration of subsequent RGDC polypeptides, and adsorption of a photosensitizer ICG are affected by many factors, for example, an addition amount of double distilled water/ethanol, reaction time of MPDA nanoparticles and aminated titanium substrates, concentration of RGDC polypeptides, and concentration and reaction time of ICG; different control conditions affect constitution of a titanium material interface with a dual function.

In this embodiment, it is stressed on investigating the addition amount of double distilled water/ethanol during the synthesis of MPDA, the reaction time of the MPDA nanoparticles and the aminated titanium substrates, the concentration of RGDC polypeptides, and the concentration and reaction time of ICG. The above results show that the mesoporous polydopamine (MPDA) nanoparticles with a uniform shape of about 200 nm in diameter can be obtained by using 60 mL of double distilled water and 65 mL of ethanol; when the concentration of the MPDA nanoparticles used is 2 mg/mL, the reaction time between the MPDA nanoparticles and the aminated titanium material is 24 h, and the stable and uniform MPDA nanoparticles can be integrated on the aminated titanium surface; when the RGDC concentration is 2 mg/mL, the ICG concentration is 10 μg/mL and the reaction time is 24 h, the titanium material Ti-M/I/RGD with a dual function is obtained.

Embodiment 2

A preparation method of a biomedical titanium implant with a function of eliminating a surface biomembrane includes the following steps:

1) Synthesize mesoporous polydopamine (MPDA) nanoparticles by a "one-pot method";

1.1) Weigh polyoxyethylene polyoxypropylene (PLURIONIC® F127 poloxamer) into a 250 mL reaction flask; weigh trimethylbenzene (TMB) into a reaction flask; pour distilled water and ethanol in sequence; and then stir a mixture of distilled water and ethanol for 10-60 min at ambient temperature;

1.2) Dissolve dopamine hydrochloride and trismetylaminomethane (Tris) in the distilled water; add the dissolved mixture to the mixed solution of Step 1.1); and make the dissolved mixture fully react with the mixed solution at ambient temperature;

In Steps 1.1) to 1.2), the ratio of the mass (mg) of polyoxyethylene polyoxypropylene to the volume (mL) of trimethylbenzene to the volume (mL) of the distilled water in Step 1.1) to the volume (mL) of ethanol to the mass (mg) of dopamine hydrochloride to the volume (mL) of trismetylaminomethane to the volume (mL) of the distilled water in Step 1.2) is (2000-4000):(2-5):(500-1000):(500-1000):(200-800):(200-1000): 100;

The reaction processes are respectively carried out at ambient temperature, with 6-24 h reaction time;

1.3) Sonicate the nanoparticles prepared by Step 1.2) for 20-60 min in a 30 mL ethanol/acetone (1:1, 1:2, 1:3) mixed solution to remove the template; and collect mesoporous polydopamine nanoparticles prepared through centrifugation.

In the Step, the ratio of ethanol to acetone is 1:(1-3).

Collect the sediments through repeated five-time centrifugation, and collect the nanoparticles prepared through centrifugation.

2) Form a large number of hydroxyl groups on the surface of the titanium material by diacid corrosion, and further modify the surface of the titanium material through amination.

2.1) Prepare a hydrofluoric acid solution with a concentration of 0.1%-0.5% and a sulfuric acid solution with a concentration of 50%-70%; mix the hydrofluoric acid solution with the sulfuric acid solution (HF:H2SO4) according to the ratio of (1-2):(1-2) to prepare a diacid solution; place a titanium foil with the size of 10 mm×10 mm into the diacid solution; and make the titanium foil fully react with the diacid solution for 5-20 min at temperature of 40-80° C. to prepare a titanium material with a large number of hydroxyl groups on the surface thereof.

2.2) Soak the titanium material prepared by Step 2.1) in a solution of 3-aminopropyltriethoxysilane (APTES) with a concentration of 1%-5%; and make the titanium material fully react with the solution for 12-48 h to prepare a aminated titanium material.

3) Integrate the MPDA nanoparticles into the surface of the aminated titanium material through Michael addition reaction.

3.1) Disperse the mesoporous polydopamine nanoparticles prepared by Step 1.3) into Tris-HCl with a pH value of 7-9, to prepare an MPDA solution with a concentration of 1-5 mg/mL.

3.2) Soak the aminated titanium material prepared by Step 2.2) in the MPDA solution and make the aminated titanium material react with the MPDA solution for 12-24 hours, to prepare a Ti-M substrate.

4) Integrate RGDC polypeptides on the surfaces of the MPDA nanoparticles through Michael addition reaction and load a photosensitizer ICG into MPDA on the surface of the titanium material through π-π stacking interaction.

4.1) Prepare a 1-5 mg/mL RGDC polypeptide solution, and take a Tris-HCl solution with a pH value of 7-9 as a solvent; soak the Ti-M substrate prepared by Step 3.1) in the RGDC solution; and make the Ti-M substrate fully react with the RGDC solution, to prepare a Ti-M/RGD substrate.

4.2) Prepare a 2-20 μg/mL indocyanine green (ICG) solution with distilled water as a solvent; soak the Ti-M/RGD substrate prepared by Step 4.1) into the ICG solution, make the Ti-M/RGD substrate fully react with the ICG solution for 12-24 h, and finally prepare a non-invasive functional titanium material for eliminating the biomembrane and accelerating bone formation with a photothermal/photodynamic effect triggered by a long-range near-infrared light (NIR), where the titanium material is referred to as Ti-M/I/RGD.

Experiment 1

Efficiency detection and observation of viable and devitalized staining are carried out for the material surface anti-biomembrane according to the embodiment 1.

The diluted *Staphylococcus aureus* (*S. aureus*) is inoculated into different material surfaces with the density of $1×10^6$ cells/pore and cultured for 48 hours at temperature of 37° C. to form a biomembrane on the different material surfaces; and then different samples are exposed to a 808 nm near-infrared laser for 10 minutes.

In order to test the anti-biomembrane efficiency of different material surfaces, different titanium materials are taken out, and rinsed gently with PBS three times to wash away devitalized bacterium; and then the titanium materials are added with 1 ml PBS and subject to sonication, to detach an adhesive biomembrane. The titanium materials again subject to sonication for 10 minutes are gradually diluted; 50 µL of the diluted bacterial solution is absorbed, spread on an MHB solid medium, and cultured for 18 hours at temperature of 37° C.; the number of bacterial colonies in different groups is counted as a control group; and finally the pure titanium materials are treated with infrared lights (Ti+NIR) under stimulation of near-infrared lights. Ti-M/+NIR (50° C.), Ti-M/RGD+NIR (50° C.), and Ti-M/I/RGD+NIR (50° C.) indicate that the materials are heated up to 50° C. under stimulation of near-infrared lights, and Ti-M/RGD+NIR (37° C.) indicates that the materials are heated up to 37° C. under stimulation of near-infrared lights.

In order to prepare viable and devitalized staining samples for fluorescence microscope observation, a 4% paraformaldehyde solution is firstly used for securing bacterium for 30 minutes at temperature of 4° C., and the biomembranes on the different material surfaces are respectively stained for 20 minutes with a hybird staining solution SYTO9 and a PI stain (which is an viable/devitalized bacterial staining kit). Viable bacterium and devitalized bacterium are stained green and red respectively. After viable bacterium and devitalized bacterium stained are washed with PBS 3 times, the survival of bacterium in the biomembrane is observed with an inverted fluorescence microscope.

Figure 5:
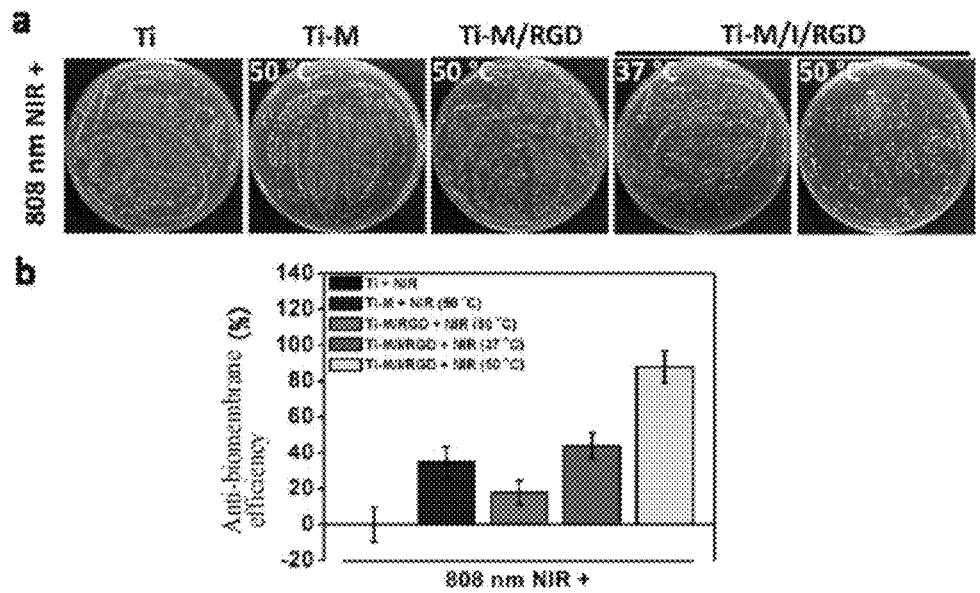
FIG. 5 is a representative plate picture (5a) after a *Staphylococcus aureus* (*S. aureus*) biomembrane is treated on different substrate surfaces in different ways and an anti-biomembrane efficiency evaluation (5b)

FIG. 5a is a flat picture of remaining viable bacterium on the material surfaces after the *Staphylococcus aureus* (*S. aureus*) biomembranes on different samples are exposed to near-infrared lights; and FIG. 5b is quantified anti-biomembrane efficiency. In the evaluation of anti-biomembrane efficiency, after Ti-M+NIR (50° C.), Ti-M/RGD+NIR (50° C.), Ti-M/I/RGD+NIR (37° C.) and Ti-M/I/RGD+NIR (50° C.) are exposed for 10 min under near-infrared lights, the anti-biomembrane efficiency thereof is respectively up to 34.7%, 17.7%, 43.9%, and 87.9%.

Figure 6:
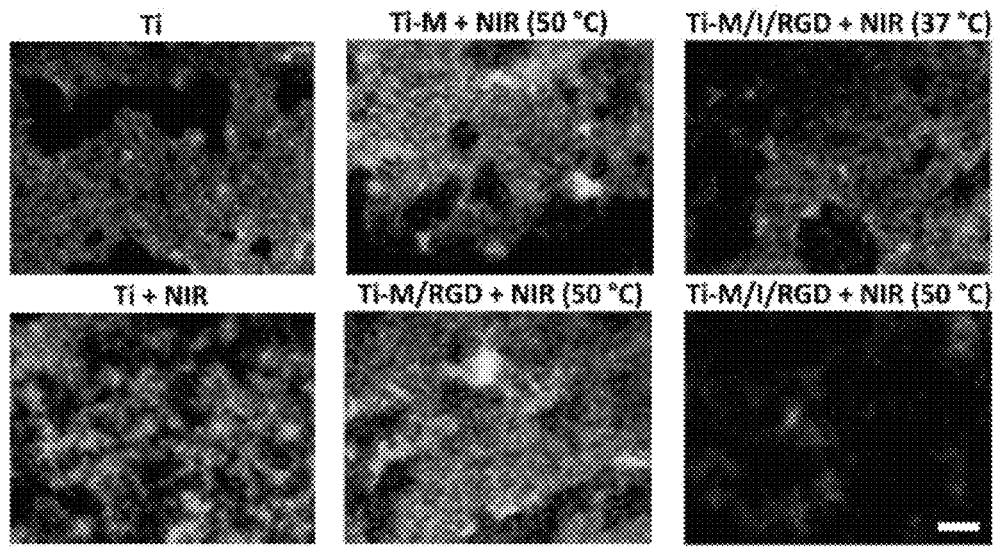
FIG. 6 is an viable and devitalized staining situation after a *Staphylococcus aureus* (*S. aureus*) biomembrane is treated on different substrate surfaces in different ways.

The biomembrane viable/devitalized staining as shown in FIG. 6 is used for further evaluating the anti-biomembrane effect, where the viable bacterium in an intact biomembrane and the devitalized bacterium in a sensitive biomembrane are respectively stained green and red under a fluorescence microscope. *Staphylococcus aureus* in Ti and Ti+NIR groups is almost no red fluorescence, indicating the viable bacterium in the biomembranes. However, Ti-M+NIR (50° C.), Ti-M/RGD+NIR (50° C.) and Ti-M/I/RGD+NIR (37° C.) groups show some red fluorescence, and Ti-M/I/RGD+NIR (50° C.) group shows more red fluorescence. The viable/devitalized staining results show that Ti-M/I/RGD+NIR (50° C.) has effective anti-biomembrane performance consistent with that shown in the plate diffusion results.

Figure 7:
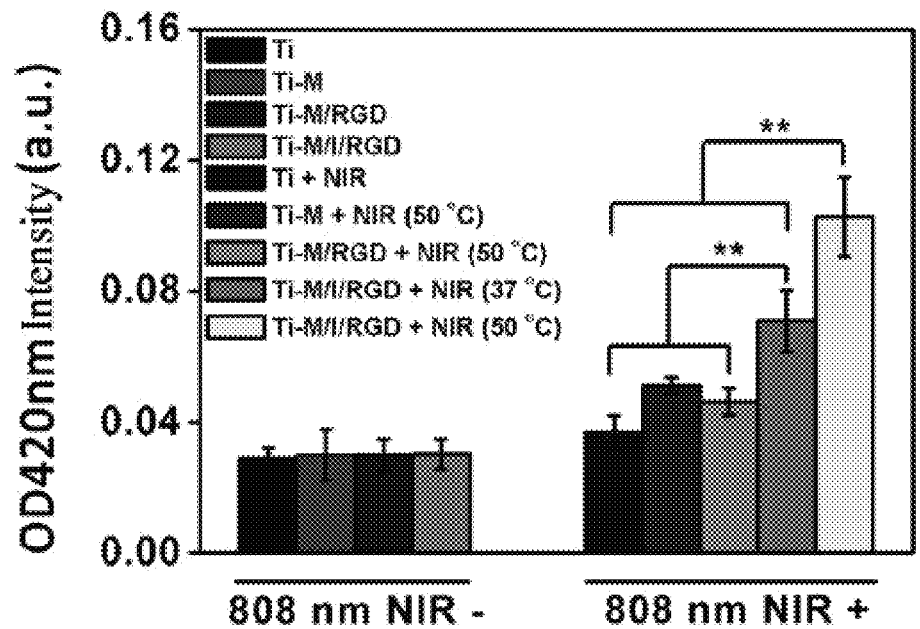
FIG. 7 is a change curve in permeability of a *Staphylococcus aureus* (*S. aureus*) bacterial membrane tested by 2-Nitrophenyl β-D-galactopyranoside (ONPG) after a biomembrane is treated on different substrate surfaces in different ways.

In addition, in FIG. 7, the cell membrane permeability of *Staphylococcus aureus* is embodied by 2-Nitrophenyl β-D-galactopyranoside (ONPG), thereby reflecting the extent of bacterial membrane damage under a PDT/PTT effect. The more severe bacterial membrane damage indicates the stronger permeability of ONPG to *Staphylococcus aureus*. The β-d-galactosidase in the bacterium is used to catalyze ONPG permeating in the bacterium to generate o-nitrophenol which can be tested within a position of 420 nm by the ultraviolet and visible spectrophotometer. After Ti-M/I/RGD+NIR (37° C.), Ti-M+NIR (50° C.) and Ti-M/RGD+NIR (50° C.) groups are exposed to near-infrared lights, hydrolysis of ONPG in the Ti-M/I/RGD+NIR (37° C.) group is significantly increased when being compared to those in the Ti-M+NIR (50° c.) and Ti-M/RGD+NIR (50° C.) groups ($p<0.01$), indicating that the membrane damage of ROS to *Staphylococcus aureus* in the biomembrane is more severe than that in separate use of lights and heat. The Ti-M/I/RGD+NIR (50° C.) group shows the strongest ONPG hydrolysis ability and has the most effective ability to destroy the bacterial membranes when being compared to other groups.

To be specific, under stimulation of near-infrared lights (NIR), the ROS generated by ICG can cause damage to the bacterial membrane in the biomembrane, and the bacterium are very sensitive to high temperature (50° C.) generated by stimulating MPDA with the near-infrared lights, thereby exerting a photothermal/photodynamics anti-biomembrane effect.

Experiment 2

Viability detection and alkaline phosphatase detection are carried out for mesenchymal stem cells (MSCs) on the surfaces of the materials obtained according to the embodiment 1. [0100] When the cells grow to a third-generation one, the cells are inoculated onto different titanium surfaces (Ti, Ti-M, Ti-M/RGD, and Ti-M/I/RGD) and TCPS with the density of $2\times10^4$ cells/pore, cultured for different time under the conditions of 37° C. and 5% $CO_2$, and changed for a medium every two days.

The cell viability on the surfaces of different materials cultured for 4 days and 7 days is tested by a CCK-8 technology; at different time points, in order to test the cell viability on the surfaces of different materials, a 200 µL culture medium without including serum and a 20 µL CCK-8 solution are added into each pore after an old culture medium is absorbed, continue to be cultured for 1.5 h, and then are measured for light absorption values of each group at 450 nm.

In addition, the alkaline phosphatase levels of the cells on the surfaces of different materials cultured for 4 days and 7 days are tested by a BCA kit and an alkaline phosphatase kit; at different time points, the total protein content in different groups of cells is determined by the BCA kit; and light absorption values of different groups at a position of 520 nm are determined by an ALP kit, and the ALP viability of each group is calculated according to the formula.

Figure 8:
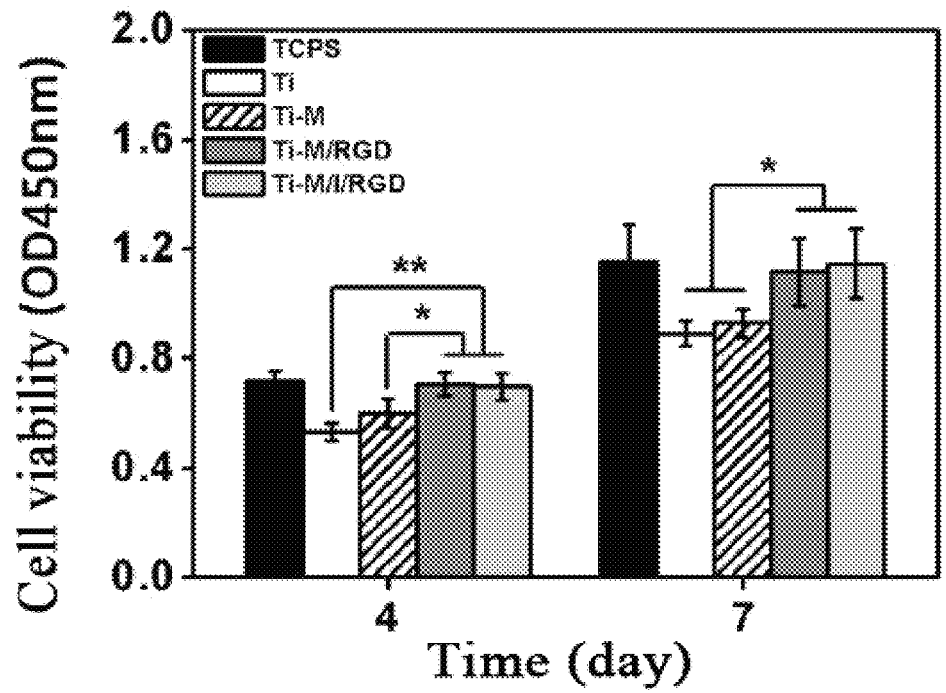
FIG. 8 is a cell viability graph of mesenchymal stem cells (MSCs) that are on the surfaces of different modified samples and cultured for 4 days and 7 days.

Cell AKP viability(U/g prot)=(measured OD value-blank OD value)/(standard OD value-blank OD value)×standard concentration(0.1 mg/mL)÷protein concentration(gprot/mL) of to-be-tested sample;

FIG. 8 is a cell viability graph of mesenchymal stem cells that are on the surfaces of the samples and cultured for 4 days and 7 days. Referring to FIG. 8, it can be seen that after the cells are cultured in two periods (4 days and 7 days), the cell viability on the surfaces of Ti and Ti-M materials is significantly lower than that of the Ti-M/RGD and Ti-M/I/RGD groups, and the cell viability of the Ti-M/RGD and Ti-M/I/RGD groups is not significantly different.

Figure 9:
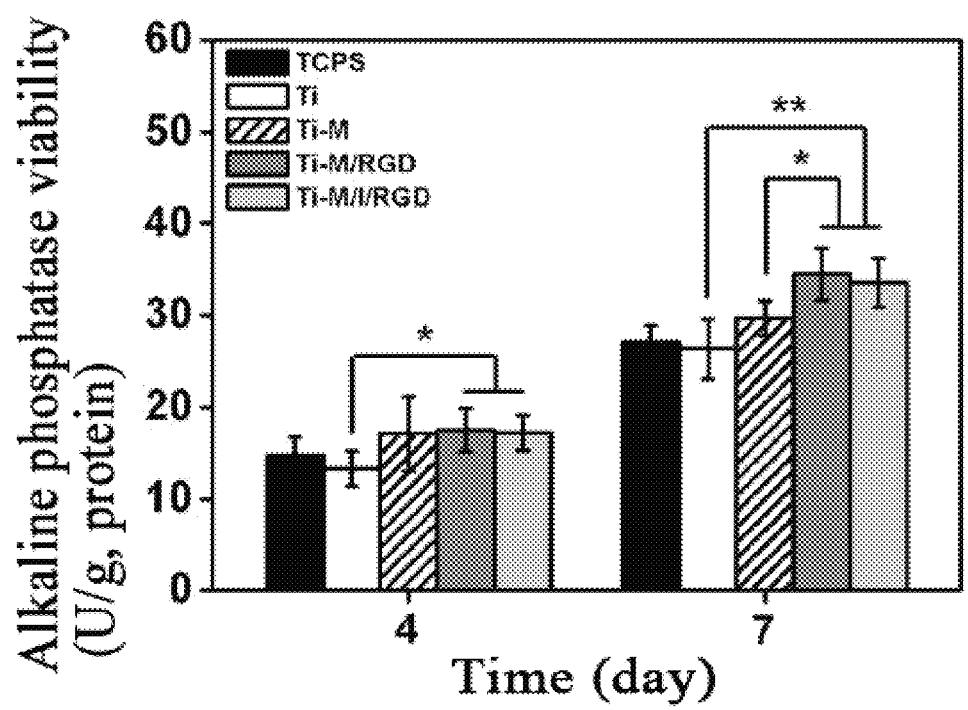
FIG. 9 is an alkaline phosphatase viability graph of mesenchymal stem cells (MSCs) that are on the surfaces of different modified samples and cultured for 4 days and 7 days.

FIG. 9 is an alkaline phosphatase viability graph of mesenchymal stem cells (MSCs) that are on the surfaces of different samples and cultured for 4 days and 7 days. Referring to FIG. 9, it can be seen that, regardless of 4 days or 7 days, the alkaline phosphatase viability on Ti-M/RGD and Ti-M/I/RGD surface cells is significantly higher than that of Ti and Ti-M groups.

In conclusion, no special equipment is provided in the preparation method, and the preparation method is simple to operate, and has strong controllability; in the present invention, a preparation method of a titanium material constituted based on a photothermal/photodynamics therapy strategy

The invention claimed is:

1. A preparation method of a biomedical titanium implant with a function of eliminating a surface biomembrane, comprising the following steps:
   1) synthesizing mesoporous polydopamine (MPDA) nanoparticles;
   1.1) weighing polyoxyethylene polyoxypropylene oxide into a reactor; weighing trimethylbenzene (TMB) into a reaction flask; pouring distilled water and ethanol in sequence; and then stirring a mixture of distilled water and ethanol at ambient temperature to form a mixed solution;
   1.2) dissolving dopamine hydrochloride and trismetylaminomethane (Tris) in distilled water to form a dissolved mixture; adding the dissolved mixture to the mixed solution of Step 1.1); and making the dissolved mixture fully react with the mixed solution at ambient temperature;
   1.3) carrying out centrifugal treatment on a product prepared after reaction in Step 1.2), wherein sediments prepared through centrifugal treatment are non-mesoporous polydopamine nanoparticles; dispersing the nanoparticles in a mixture of ethanol and acetone; removing a template through sonication; and collecting prepared mesoporous polydopamine nanoparticles through centrifugation; wherein the ratio of ethanol to acetone is 1:(1-3);
   2) forming a large number of hydroxyl groups on the surface of a titanium material by diacid corrosion, and further modifying the surface of the titanium material through amination;
   2.1) preparing a diacid solution consisting of hydrofluoric acid and sulfuric acid; placing a titanium foil into the diacid solution; and making the titanium foil fully react with the diacid solution to prepare a titanium material with a large number of hydroxyl groups on the surface thereof;
   2.2) soaking the titanium material prepared by Step 2.1) in a solution of 3-aminopropyltriethoxysilane (APTES); and making the titanium material fully react with the solution of 3-aminopropyltriethoxysilane (APTES) to prepare a aminated titanium material;
   3) integrating the MPDA nanoparticles into the surface of the aminated titanium material through Michael addition reaction;
   3.1) dispersing the mesoporous polydopamine nanoparticles prepared by Step 1.3) into Tris-HCl with a pH value of 7-9, to prepare an MPDA solution;
   3.2) soaking the aminated titanium material prepared by Step 2.2) in the MPDA solution and making the aminated titanium material react with the MPDA solution for 12-24 hours, to prepare a Ti-M substrate;
   4) integrating RGDC polypeptides on the surfaces of the MPDA nanoparticles through Michael addition reaction and loading a photosensitizer ICG into MPDA on the surface of the Ti-M substrate through π-π stacking interaction;
   4.1) preparing a 1-5 mg/mL RGDC polypeptide solution, and taking a Tris-HCl solution with a pH value of 7-9 as a solvent; soaking the Ti-M substrate prepared by Step 3.2) in the RGDC solution; and making the Ti-M substrate fully react with the RGDC solution, to prepare a Ti-M/RGD substrate;
   4.2) preparing a 2-20 μg/mL indocyanine green (ICG) solution with distilled water as a solvent; soaking the Ti-M/RGD substrate prepared by Step 4.1) in the ICG solution, making the Ti-M/RGD substrate fully react with the ICG solution, and finally preparing the biomedical titanium implant for eliminating the biomembrane and accelerating bone formation with a photothermal/photodynamic effect triggered by a non-invasive long-range near-infrared light (NIR), wherein the biomedical titanium implant is referred to as Ti-M/I/RGD.

2. The preparation method of a biomedical titanium implant with a function of eliminating a surface biomembrane according to claim 1, wherein in Step 1), the mesoporous polydopamine (MPDA) nanoparticles are synthesized by a one-pot method.

3. The preparation method of a biomedical titanium implant with a function of eliminating a surface biomembrane according to claim 2, wherein the mixture of distilled water and ethanol in Step 1) is required to be stirred for 10-60 minutes at ambient temperature.

4. The preparation method of a biomedical titanium implant with a function of eliminating a surface biomembrane according to claim 2, wherein the reaction in Step 1.2) is carried out at ambient temperature, with the reaction time ranging from 6-24 h.

5. The preparation method of a biomedical titanium implant with a function of eliminating a surface biomembrane according to claim 2, wherein in Step 1.3), sonication is carried out for 20-60 min to remove the template, and collection of sediments through centrifugation is repeatedly conducted 1-5 times to collect nanoparticles generated through centrifugation.

6. The preparation method of a biomedical titanium implant with a function of eliminating a surface biomembrane according to claim 1, wherein in Step 2.1), the reaction temperature is in the range of 40-80° C., and the reaction time is in the range of 5-20 min.

7. The preparation method of a biomedical titanium implant with a function of eliminating a surface biomembrane according to claim 1, wherein in Step 2.1), the size of the titanium foil is 10 mm×10 mm; in Step 2.2), the reaction time is in the range of 12-48 h.

8. The preparation method of a biomedical titanium implant with a function of eliminating a surface biomembrane according to claim 1, wherein in Steps 4.1) and 4.2), the reaction time is in the range of 12-24 h.

9. The preparation method of a biomedical titanium implant with a function of eliminating a surface biomembrane according to claim 1, wherein different titanium materials in Steps 2.1), 2.2), 4.1) and 4.2) are required to be rinsed with distilled water 3 times and dried at ambient temperature.

10. A titanium material prepared by the preparation method according to claim 1, wherein the biomedical titanium implant is used for eliminating a biomembrane formed on the surface of the biomedical titanium implant based on a photothermal/photodynamic therapy strategy.

* * * * *